(12) United States Patent
Sawa et al.

(10) Patent No.: US 6,618,137 B1
(45) Date of Patent: Sep. 9, 2003

(54) ELASTIC FINE TUBE, ITS PRODUCTION PROCESS AND PARTICLE ANALYZER USING THE ELASTIC FINE TUBE

(75) Inventors: Kenichi Sawa, Osaka (JP); Fumio Kubota, Nishinomiya (JP)

(73) Assignee: Sysmex Corporation, Hyogo (JP)

( * ) Notice: Subject to any disclaimer, the term of this patent is extended or adjusted under 35 U.S.C. 154(b) by 0 days.

(21) Appl. No.: 09/714,141

(22) Filed: Nov. 17, 2000

(30) Foreign Application Priority Data

Nov. 18, 1999 (JP) .......................................... 11-370778

(51) Int. Cl.⁷ .............................................. G01N 21/05
(52) U.S. Cl. ...................... 356/246; 356/335; 356/336; 356/337; 356/338; 356/432; 356/436
(58) Field of Search ................................ 356/246, 432, 356/436, 441, 442, 335, 336, 337, 338

(56) References Cited

U.S. PATENT DOCUMENTS 5,404,217 A * 4/1995 Janik et al. .................. 356/246
5,414,508 A * 5/1995 Takahashi et al. .......... 356/246

FOREIGN PATENT DOCUMENTS

JP             6-52265              7/1994

* cited by examiner

*Primary Examiner*—John R. Lee
*Assistant Examiner*—David A. Vanore
(74) *Attorney, Agent, or Firm*—Birch, Stewart, Kolasch & Birch, LLP

(57) ABSTRACT

An elastic fine tube includes a light-transmissive body of an elastic material having at least one flow channel therethrough, and a first connecting conduit and a second connecting conduit connected to the body and communicating with both ends of the inside flow channel of the body, respectively.

13 Claims, 9 Drawing Sheets

ELASTIC FINE TUBE, ITS PRODUCTION PROCESS AND PARTICLE ANALYZER USING THE ELASTIC FINE TUBE

CROSS-REFERENCE TO RELATED APPLICATION

This application is related to Japanese Patent Application No. Hei 11(1999)-370778 filed on Nov. 18, 1999, whose priority is claimed under 35 USC §119, the disclosure of which is incorporated by reference in its entirety.

BACKGROUND OF THE INVENTION

1. Field of the Invention

The present invention relates to an elastic fine tube which is light-transmissive and flexible and which has a fine flow channel, its production process and an analyzer using the elastic fine tube.

2. Description of Related Art

A sheath flow cell has been generally utilized in blood cell counters because it serves to detect blood cells one by one without coincidence loss of the blood cells. The sheath flow cell means a cell which defines a fine sample flow that is hydrodynamically focused in a sheath liquid and that has a diameter of several tens of micrometers. If a tube as fine as the sample flow can be produced, then it will be possible to detect separate blood cells one by one without utilizing the sheath flow cell.

With recent development of a micro-machining technique, fine flow channels are increasingly formed by etching. This technique enables the formation of flow channels having a rectangular cross section with a side of several micrometers to several hundreds of micrometers. However, the flow channels, when used for blood cell counters, need to be provided with affinity for blood cells coming from living bodies by treating their inside walls with coating or the like.

Besides, the flow channels formed by the micro-machining technique inevitably have undulations on the inside walls. For this reason, fine particles that are flown in the flow channels adhere to the undulations, and smooth flow of the particles cannot be obtained. In addition, a huge investment in a plant and equipment is required for implementing this technique.

On the other hand, commercially available are various kinds of fine tubes made of silicone, Teflon and others. However, the commercially available tubes are limited in size, and the smallest ones are about 0.5 mm in internal diameter and 1 mm in external diameter.

Japanese Patent Publication No. HEI 6(1994)-52265 discloses a technique for producing a tube by extrusion molding and changing the tube into a finer tube by heating and stretching.

However, the formation of a tube by extrusion and stretching involves quenching, and residual stress makes it extremely difficult to obtain a transparent tube with a small birefringence. It is inherently difficult to produce an fine tube of a elastic material such as silicone rubber by stretching.

SUMMARY OF THE INVENTION

The present invention has been made in view of the above-mentioned circumstances, and an object of the invention is to provide an elastic fine tube which is light-transmissive and flexible and has a fine flow channel therethrough. Also the invention provides a process of producing the elastic fine tube as well as an analyzer using the elastic fine tube.

The elastic fine tube of the present invention is characterized by including a light-transmissive body of an elastic material having at least one flow channel therethrough so that a particle not more than 300 μm in diameter passes through the flow channel, and a first connecting conduit and a second connecting conduit which are connected to the body and communicated with both ends of the flow channel of the body, respectively.

The process of producing the elastic fine tube of the present invention is a process of producing an elastic fine tube which includes a light-transmissive body of an elastic material having at least one flow channel therethrough and a first connecting conduit and a second connecting conduit which are connected to the body and communicated with both ends of the flow channel of the body, respectively, the process comprising the steps of preparing a mold having at least one elongated groove passing both ends of an elongated core through the first and second connecting conduits respectively supporting the first and second connecting conduits at both ends of the groove in such a manner that the first and second connecting conduits and the core are substantially coaxial with respect to a longitudinal axis of the groove of the mold and one end of each of the first and second connecting conduits is rested in the groove pouring a fluid polymer resin to be cured into the groove of the mold curing the fluid polymer resin to form a molded form taking the molded form out of the mold and taking the core out of the molded form.

Further, the particle analyzer of the invention is characterized by including the above elastic fine tube; a liquid feed section for feeding a particle suspension into the elastic fine tube; and a detection section for measuring optical information of particles running through the elastic fine tube.

These and other objects of the present application will become more readily apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DESCRIPTION OF THE PREFERRED EMBODIMENTS

The elastic material in the present invention may be a natural rubber or a synthetic rubber. As examples of synthetic rubbers, may be mentioned materials containing, as a main ingredient, a silicone resin, a butylated resin, a nitrile resin, a chloroprene resin, an SBR, an ethylene-propylene terpolymer rubber or the like. Preferably, the elastic material is a silicone rubber. Accordingly, the elastic fine tube using the elastic material is elastically deformable and has a high affinity for blood cells. Therefore, the elastic fine tube hardly damages blood cells passing through its flow channel.

The connecting conduits may be constructed of a tubular rigid material, for example, of a metal, a rigid resin, glass or the like. As regards the metal, it is preferable to use a corrosion-resistant stainless steel. As regards the rigid resin, it is preferable to use a polyacetal resin, a polycarbonate resin, Teflon resin, a nylon resin, a polyester resin, a fluorine resin, a silicone resin, a phenolic resin, an amino resin, an epoxy resin and the like, which have good moldability and workability. Commercially available injection needles may be used as the connecting conduits.

The elastic fine tube may be constructed to have one inside flow channel or a plurality of inside flow channels which may be arranged in parallel or arranged to cross each other.

Preferably, the elastic fine tube is composed of a light-transmissive body of an elastic material having one flow channel therethrough, and a first connecting conduit and a second connecting conduit which are connected to the body and communicated with both ends of the flow channel of the body, respectively.

Preferably, the flow channel of the elastic fine tube has a circular cross section with an internal diameter of 10 to 300 $\mu$m, more preferably 30 to 50 $\mu$m. The thickness of the elastic fine tube is preferably 0.1 to 5 mm, more preferably 0.5 to 2 mm.

The body of the elastic fine tube may have a circular, elliptical or quadrangular cross section. A body with a quadrangular cross section is advantageous because the elastic fine tube can be placed in a stable state.

The core may be formed of a metal and may preferably be a stainless steel wire or a tungsten wire. It is particularly preferable to use a tungsten wire with an external diameter of 10 to 300 $\mu$m. Since tungsten has a small distortability, it is possible to produce a wire with an accurate external diameter. Also since tungsten has a high tensility, it is not cut off when pulled out of a mold. For these reasons, tungsten can provide a flow channel of stable diameter if used for the production of the elastic fine tube. A tungsten wire having a rectangular cross section may also be used.

The mold may be constructed of a metal, a rigid resin or glass. As regards the metal, it is preferable to use a corrosion-resistant stainless steel. As regards the rigid resin, it is preferable to use a polyacetal resin, a polycarbonate resin, Teflon resin, a nylon resin, a polyester resin, a fluorine resin, a silicone resin, a phenolic resin, an amino resin, an epoxy resin and the like, which have good moldability and workability.

In the process of producing the elastic fine tube, to first carry out the step of inserting the core into the connecting conduits facilitates the step of holding the connecting conduits in such a manner that one end of each of the connecting conduits is rested in the groove of the mold at an end portion of the mold. For it is not easy to insert the core through the connecting conduits after the connecting conduits are rested on the mold.

In the step of pouring the fluid polymer resin or fluid rubber material in the mold, an injection syringe, a dispenser or the like may be used.

The fluid polymer resin may be a rubber before curing which has fluidity, for example. The rubber may be a natural rubber or a synthetic rubber. Examples of synthetic rubbers include synthetic rubbers containing as a main ingredient a silicone resin, a butylated resin, a nitrile resin, a chloroprene resin, an SBR, an ethylene-propylene terpolymer resin or the like, and the silicone resin may be suitable. The resin may be cured thermally, by use of a curing agent, or the like.

The thus completed elastic fine tube can suitably be used for observation and determination of blood cells, particles in urine and biological particles such as cultured cells, microorganisms, plankton and the like. Also it may be used for observation and determination of industrial particles such as a fine ceramic, a toner, a pigment, a grinder and the like.

In the particle analyzer using the elastic fine tube of the invention, a positive or negative pressure pump such as a syringe pump, a peristaltic pump, a gear pump, an air pump or the like may be used for the liquid feed section for feeding a particle suspension to the elastic fine tube. If the positive pressure pump is used, the flow channel of the elastic fine tube is distended, so that particles pass through it easily. The negative pressure pump can also feed a sample, but the flow channel of the elastic fine tube may be blocked. For this reason, the positive pressure pump is preferably used for the liquid feed section in view of easy passage of particles.

The detection section may be composed of a light source and an optical detector for measuring optical information from particles illuminated by the light source. In this case, the optical information means information about forward or side scattered light, or fluorescent light from the particles, also including information about the light emission intensity, light emitting time (pulse width) or the like. Accordingly, it is preferable to use a light source which emits continuous light, for example, a laser light source. A photodiode, a phototransistor, a photomultiplier tube and the like may be used as the optical detector.

The detection section may also be composed of an image capture device which is a combination of an illumination light source for illuminating particles in a sample liquid and a camera for capturing an image of the illuminated particles. In this case, a strobe or a pulse laser light source which intermittently emits light is preferably used as the illumination light source. A light source which continuously emits light may be used as the illumination light source, but in this case, the camera is required to be provided with a shutter means. A video camera may be used as the camera.

EXAMPLE

Figure 1:
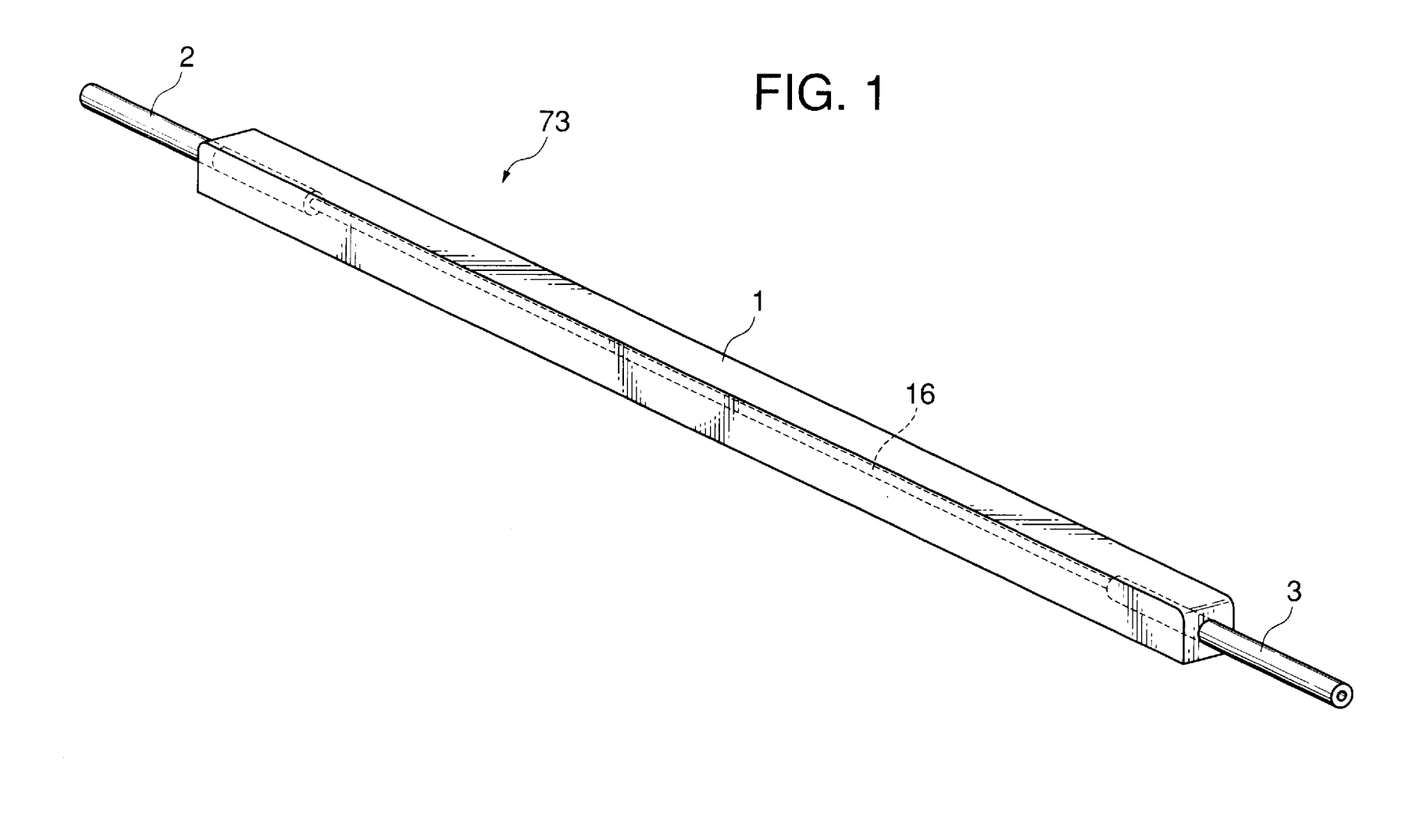
FIG. 1 is a perspective view showing the appearance of an elastic fine tube in accordance with the present invention.

FIG. 1 shows the appearance of an example of an elastic fine tube 73 in accordance with the present invention. In the figure, there are shown a transparent body 1 of a silicone rubber which has a circular inside flow channel 16 of 30 $\mu$m internal diameter and which has a square cross section of 2 mm×2 mm and a length of 110 mm, and connecting conduits 2 and 3 of stainless steel which are connected to both ends of the body 1 and which have an internal diameter of 190 $\mu$m, an external diameter of 410 $\mu$m and a length of 15 mm.

Figure 3:
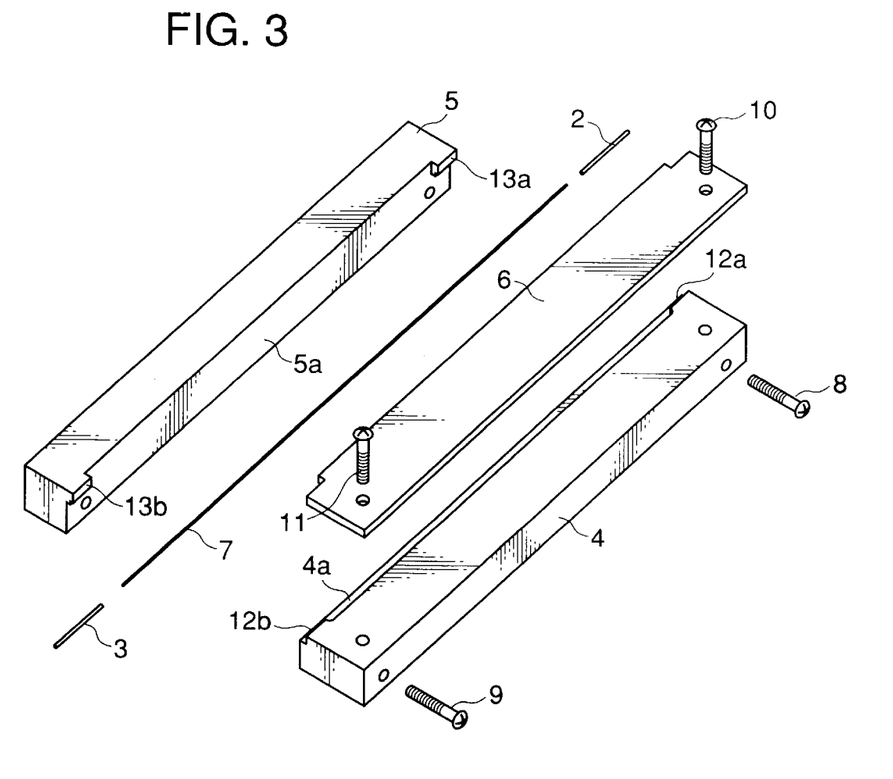
FIG. 3 is an exploded perspective view illustrating the construction of a mold.

Next, explanation is given of the process of producing the elastic fine tube which utilizes a cast molding technique. As shown in FIG. 3, a mold used in the present invention is made of stainless steel and is composed of rectangular mold components 4 and 5 and a plate-like mold component 6. When the mold components 4 and 5 are connected with screws 8 and 9, an elongated groove 15 with a square cross section as shown in FIG. 4 is defined between an elongated depression 4a with an L-shaped cross section formed along a ridge of the mold component 4 and a side wall 5a of the mold component 5.

Figure 2:
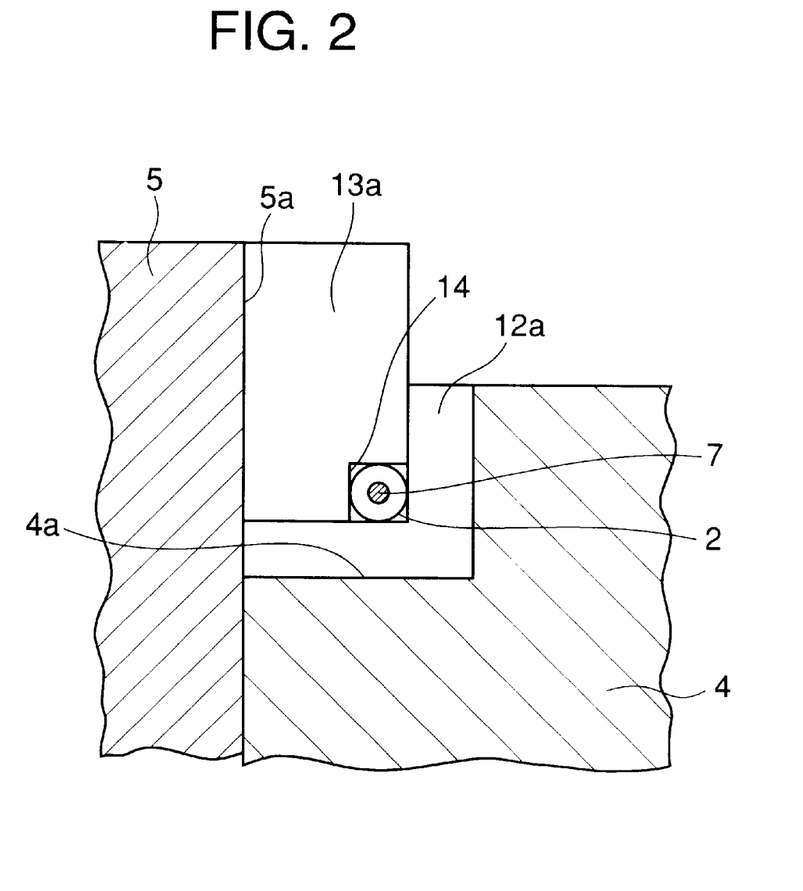
FIG. 2 is a sectional view as seen in the direction of arrow A of FIG. 4.
Figure 9:
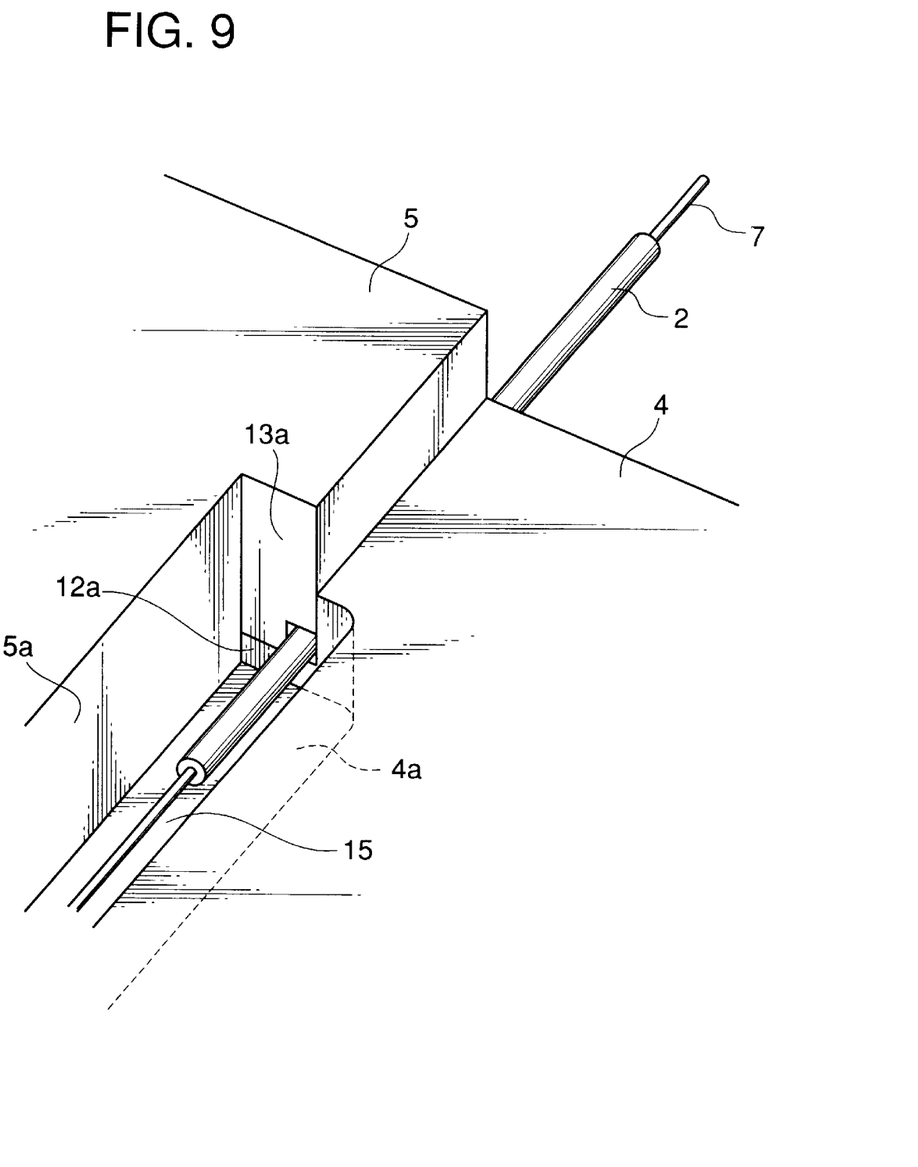
FIG. 9 is an enlarged view of a part B in FIG. 4.

Before combining the mold components 4 and 5, both ends of a tungsten wire 7 (W31-CS manufactured by Hitachi Cable Ltd., Japan; external diameter : 30 µm; length : 200 mm) is inserted in the connecting conduits 2 and 3, which are then rested on both ends of the mold component 4. Subsequently the mold components 4 and 5 are connected with the screws 8 and 9. Connecting conduit support sections 12a and 12b are formed at both ends of the mold component 4 as shown in FIG. 3. Connecting conduit support sections 13a and 13b are formed as opposed to the connection tube support sections 12a and 12b at both ends of the mold component 5. Therefore, when the mold components 4 and 5 are connected to each other and the groove 15 is defined, the connecting conduits 2 and 3 are held between the support sections 12a and 13a and between the support sections 12b and 13b, respectively, as shown in FIGS. 2 and 9. The connecting conduits 2 and 3 are securely fixed with one end of each of the connecting conduits projecting toward the groove 15.

Figure 4:
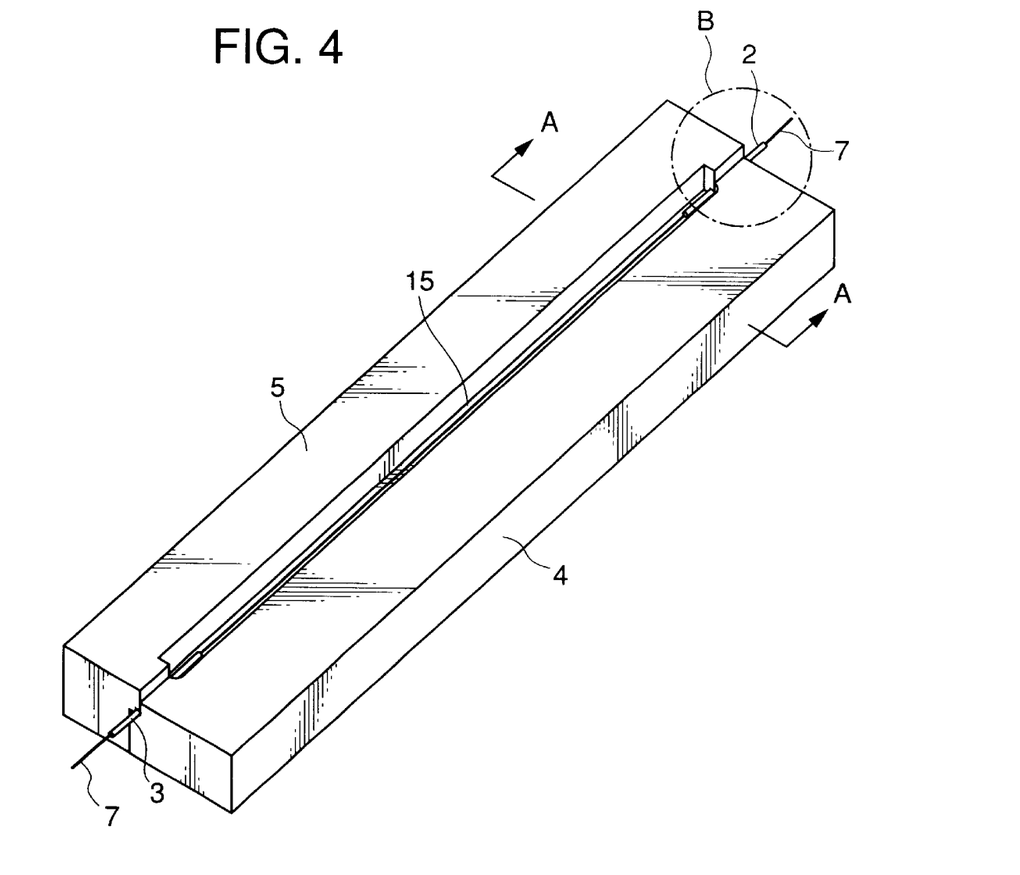
FIG. 4 is a perspective view showing the appearance of the mold before a silicone resin is poured therein.

Thereby, the connecting conduits 2 and 3 and the wire 7 are substantially coaxially fixed with respect to a longitudinal axis of the groove 15 as shown in FIGS. 4 and 9. At this time, the support section 12a and 13a and the support sections 12b and 13b also serve as walls which close both ends of the groove 15.

Figure 5:
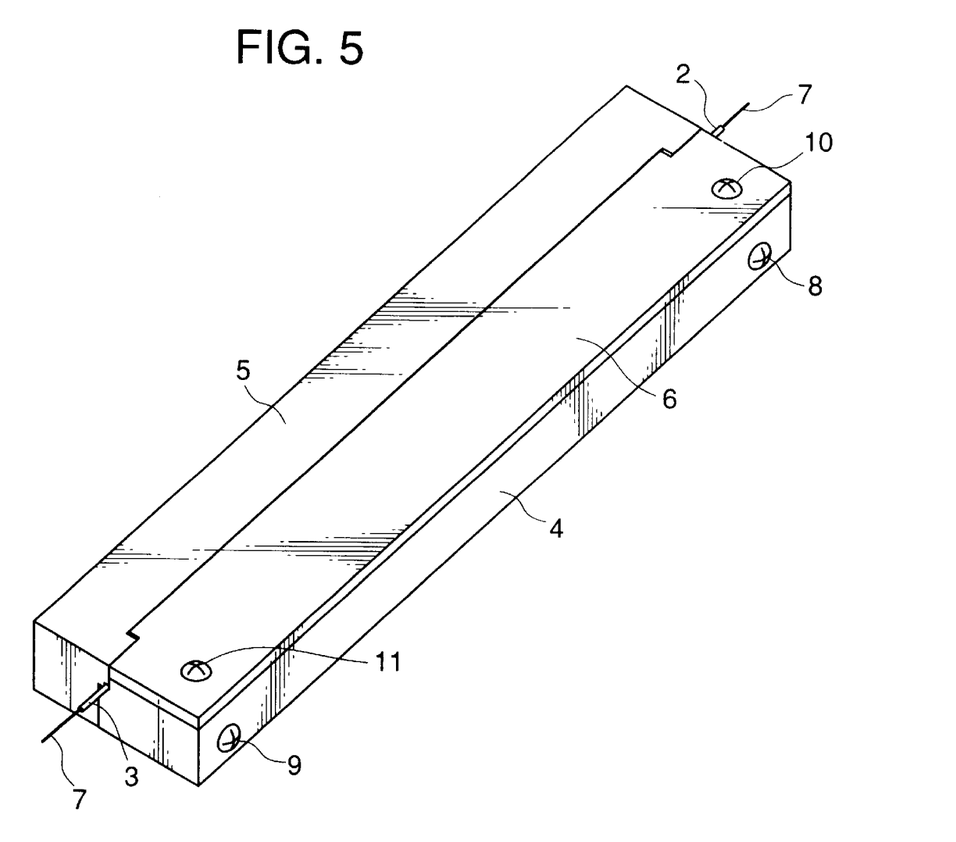
FIG. 5 is a perspective view showing the appearance of the mold after a silicone resin is poured therein.

Next, the tube 73 is molded by casting using a two-component silicone rubber (TSE3455T or TSE3450T manufactured by GE Toshiba Silicone Kabushiki Kaisha, Japan). That is, a liquid main ingredient and a liquid curing agent are mixed in a container at a given ratio. Subsequently, the container is placed in a vacuum chamber, which is deaerated for 10 minutes at an ultimate pressure of 0.13 Pa by a vacuum pump. Thereafter the container is taken out of the vacuum chamber, and the resulting mixture in the container is poured into the groove 15 along the tungsten wire 7 with use of a syringe. Then the mold component 6 is fixed with screws 10 and, 11 on the mold component 4 (see FIG. 5). This state is retained for 24 hours.

After 24 hours, all the screws 8–11 are removed from the mold components and a molded form formed in the groove 15 is taken out. By pulling the tungsten wire 7 out of the molded form, the elastic fine tube 73 highly transparent as shown in FIG. 1 is completed. If the mold components which come in contact with the body 1 are polished before molding with a lens polisher for microscopes, the body 1 of the elastic fine tube after molding has an increased transparency, which facilitates the observation of a particle suspension passing through the inside flow channel.

Figure 6:
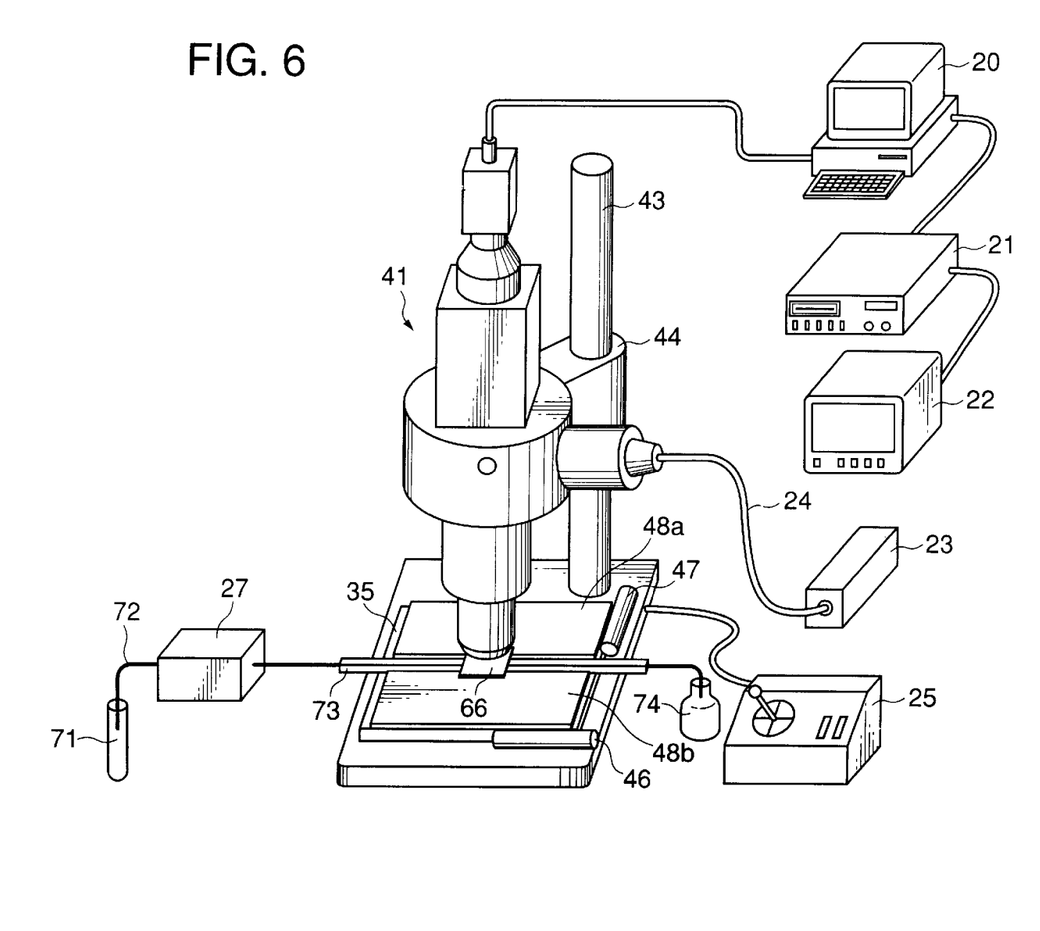
FIG. 6 is a perspective view showing the appearance of a particle analyzer in accordance with the present invention.

Now explanation is given of an example of the detection section for measuring the optical information of particles passing through the elastic fine tube of the present invention. FIG. 6 is a perspective view of an example of a particle analyzer using the elastic fine tube, and FIG. 7 illustrates the construction of the particle analyzer.

In FIG. 6, the elastic fine tube 73 is held between fixation members 48a and 48b mounted on a stage 35. A main body 41 of the analyzer is movable in a vertical direction and secured to a support rod 43 through a movable section 44. The movable section 44 is used for securing the main body 41 of the analyzer and also for putting focus for capturing images. Light from a light source 23 is supplied to the main body 41 of the analyzer by an optical fiber 24.

The stage 35 can move a site to be detected relatively to the main body 41 of the analyzer by operating an X-Y operation section 25 to actuate an X-direction actuator 46 and a Y-section actuator 47.

Figure 7:
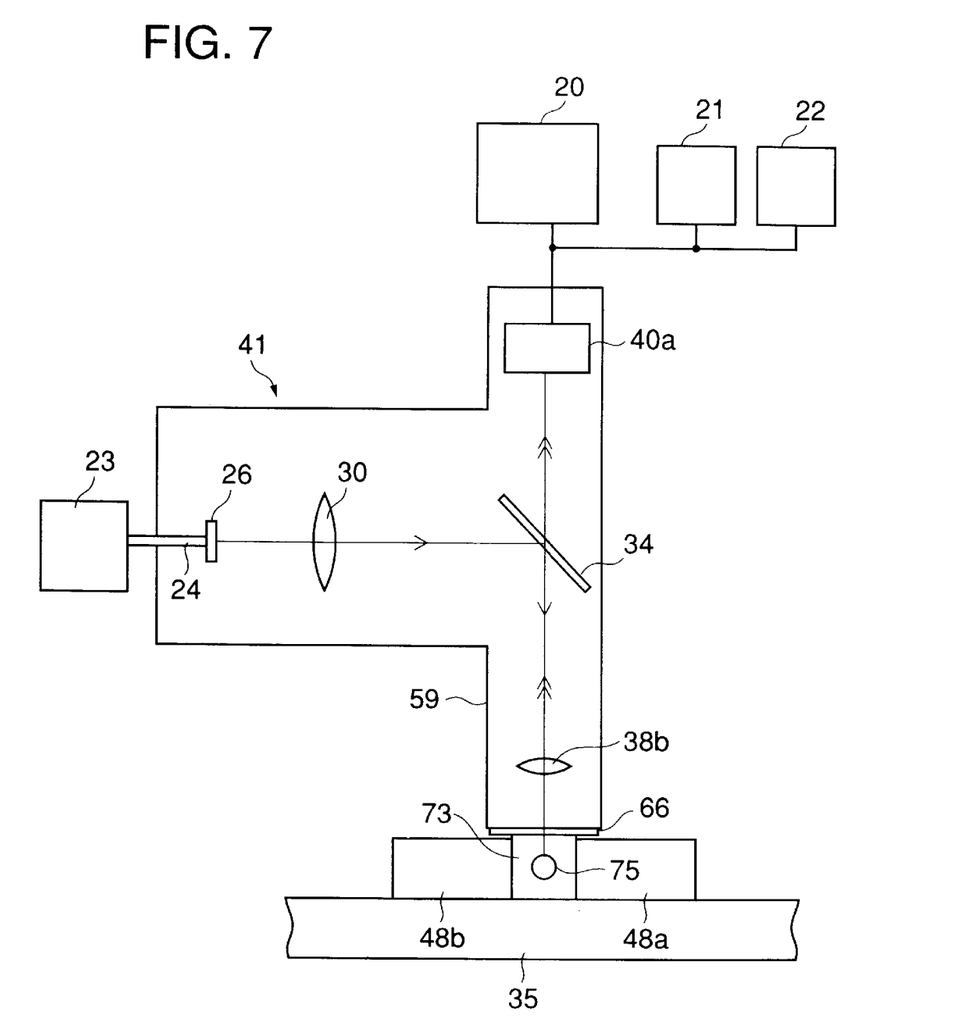
FIG. 7 illustrates the construction of the particle analyzer of FIG. 6.

In FIG. 7, light emitted from the light source 23 is directed into the main body 41 of the analyzer via the optical fiber 24 and illuminates a diffuser 26. The light is diffused by the, diffuser 26 and illuminates a sample flow 75 in the flow channel of the elastic fine tube 73 via an optical system comprised of a lens 30, a half mirror 34 and an object lens 38b and a transparent plate 66. Light from the sample flow 75 is received by a CCD 40a via the transparent plate 66, the object lens, 38b and the half mirror 34, and an image of the sample flow 75 is captured by the CCD 40a.

A blood sample 71 shown in FIG. 6 is, for example, a collected blood diluted 80 times with a physiological saline (dilution ratio of blood is preferably 5 times to 100 times). The, blood sample 71 is sucked from a suction inlet 72 and fed into the elastic fine tube 73 by a positive pressure pump 27. Blood may be diluted with a saline containing 0.5% to 2.0% acridine orange to specifically stain leukocytes, whose fluorescence image can be obtained. The sample is then stored in a waste liquid vessel 74. The captured image is supplied to an analytical device 20 for conducting image processing of various kinds, a video 21 for storing the image and a monitor 22 for real-time visualization of the image.

Figure 8:
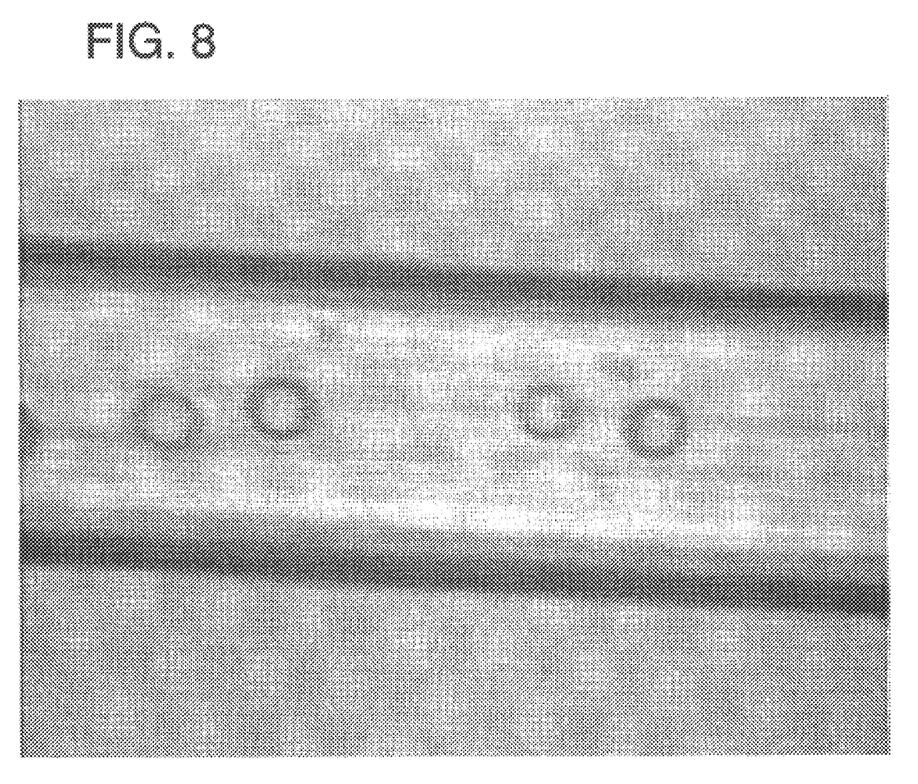
FIG. 8 shows an example of an image captured by the particle analyzer of FIG. 6.

FIG. 8 is an image of a blood sample captured by the particle analyzer shown in FIG. 6. The figure shows that blood cells flows one by one. It is possible to determine a blood cell count per unit volume of the blood sample from this image. Supposing that A denotes the number of imaged blood cells, B the length of the flow channel and C the sectional area of the flow channel, the blood cell count per unit volume is calculated by A/(B*C). For example, if A, B and C are 7, 200 µm and $(15 \mu m)^2 \times \pi$, the blood cell count is 50,000/µL. If the dilution ratio is 80 times, then the concentration of erythrocytes in the blood before dilution is 4,000,000/µL. For realizing more accurate determination of the erythrocyte concentration, images of the blood sample are preferably captured repeatedly until the total count of imaged erythrocytes reaches a certain number (for example, around 10,000).

The elastic fine tube of the present invention has light-transmissivity and flexibility and has an fine flow channel. Even if a sample to be passed through the tube is a blood sample, the elastic fine tube has high affinity for blood cells and hardly damages them. The process of producing the elastic fine tube is simple and does not require high-precision tools. The process does not involve an increase in costs for plant and equipment investment. Further, the analyzer using the elastic fine tube has a simple construction and can be made at low costs.

What is claimed is:

1. An elastic fine tube comprising:
   a light-transmissive body of an elastic material having at least one flow channel therethrough so that a particle not more than 300 µm in diameter passes through the flow channel, and
   a first connecting conduit and a second connecting conduit which are connected to the body and communicated with both ends of the flow channel of the body, respectively.

2. An elastic fine tube according to claim 1, wherein the flow channel has a circular cross section with an internal diameter of 10 to 300 µm.

3. An elastic fine tube according to claim 1, wherein the elastic material is a silicone resin.

4. An elastic fine tube according to claim 1, wherein the body has a planar external wall.

5. A particle analyzer comprising:
an elastic fine tube as set forth in claim 1;
a liquid feed section for feeding a particle suspension into the elastic fine tube; and
a detection section for measuring optical information of particles running through the elastic fine tube.

6. A particle analyzer according to claim 5, wherein the detection section includes a device for capturing an image of particles illuminated by a light source.

7. A particle analyzer comprising:
an elastic fine tube having a light-transmissive body of an elastic material having at least one inside flow channel with a circular cross section of 10 to 300 $\mu$m diameter and a first connecting conduit and a second connecting conduit which are connected to the body and communicated with both ends of the inside flow channel of the body, respectively;
a liquid feed section for feeding a particle suspension into the elastic fine tube; and
a detection section for measuring particles running through the elastic fine tube,
wherein the detection section includes a device for capturing an image of particles illuminated by a light source.

8. An elastic fine tube comprising:
a light-transmissive tubular member of a rubber having a flow channel therethrough, and
a first connecting conduit and a second connecting conduit which are inserted into both ends of the tubular member, respectively, and communicated with the flow channel.

9. An elastic fine tube according to claim 8, wherein the tubular member has a quadrangular cross section and the flow channel has a circular cross section.

10. An elastic fine tube according to claim 9, wherein the flow channel has an internal diameter of 10 to 300 $\mu$m.

11. An elastic fine tube according to claim 8, wherein the rubber is a silicone rubber.

12. A particle analyzer comprising:

an elastic fine tube as set forth in claim 8;

a liquid feed section for feeding a particle suspension to the elastic fine tube;

a light source for irradiating the elastic fine tube with light to illuminate particles; and an image capture section for capturing an image of the illuminated particles.

13. A particle analyzer comprising:

an elastic fine tube as set forth in claim 9;

a liquid feed section for feeding a particle suspension to the elastic fine tube;

a light source for irradiating an external plane of the elastic fine tube with light to illuminate particles; and an image capture section for capturing an image of the illuminated particles.

* * * * *